United States Patent [19]

Valentini et al.

[11] Patent Number: 4,576,211

[45] Date of Patent: Mar. 18, 1986

[54] SAFETY DEVICE FOR CONNECTION OF A SYRINGE WITH THE MOUTH OR OPENING OF A BOTTLE CONTAINING A DRUG OR A SMALL TUBE FOR DRUG DELIVERY FROM THE SYRINGE

[75] Inventors: Luigi Valentini, Milan; Mario Coccia, Cesano Boscone, both of Italy

[73] Assignee: Farmitalia Carlo Erba S.p.A., Milan, Italy

[21] Appl. No.: 607,502

[22] Filed: May 7, 1984

[30] Foreign Application Priority Data

Feb. 24, 1984 [IT] Italy .............................. 19785 A/84

[51] Int. Cl.$^4$ .......................... B65B 3/04; A61M 5/00

[52] U.S. Cl. .................................... 141/329; 141/372; 604/411; 604/88; 604/905; 604/201

[58] Field of Search ..................... 604/411, 86, 89, 91, 604/188, 198, 201, 205, 206, 208, 412-416, 905, 283, 88; 141/329, 330, 372, 19

[56] References Cited

U.S. PATENT DOCUMENTS

| | | | |
|---|---|---|---|
| 2,712,402 | 7/1955 | Le Clair | 141/329 |
| 3,390,677 | 7/1968 | Razimbaud | 604/414 |
| 3,739,779 | 6/1973 | Pfleger | 604/205 |
| 3,890,971 | 6/1975 | Leeson et al. | 604/198 |
| 3,977,555 | 8/1976 | Larson | 604/411 |
| 3,993,063 | 11/1976 | Larrabee | 604/414 |
| 4,180,070 | 12/1979 | Genese | 604/414 |
| 4,365,626 | 12/1982 | House | 604/206 |

FOREIGN PATENT DOCUMENTS

| | | | |
|---|---|---|---|
| 8404673 | 12/1984 | PCT Int'l Appl. | 141/330 |

*Primary Examiner*—C. Fred Rosenbaum
*Assistant Examiner*—Mark Rooney
*Attorney, Agent, or Firm*—Oblon, Fisher, Spivak, McClelland & Maier

[57] ABSTRACT

The invention relates to a device to one end of which a syringe can be connected and to the other end of which the mouth or opening of a bottle containing a drug or medicine can be connected. The device comprises a closed chamber having enclosed therein a needle which is in connection with the syringe. Members are provided by means of which the mouth or opening of the bottle is steadily connected to the device and means enabling the needle to perforate a seal plug and then a small rubber plug mounted on the bottle only when the device is blocked onto the bottle so that in any case it cannot be disconnected therefrom. Such a device can be disconnected from the bottle only after the needle has been caused to reenter the closed chamber, so as to prevent any possible dripping of the liquid outside of the device.

8 Claims, 6 Drawing Figures

SAFETY DEVICE FOR CONNECTION OF A SYRINGE WITH THE MOUTH OR OPENING OF A BOTTLE CONTAINING A DRUG OR A SMALL TUBE FOR DRUG DELIVERY FROM THE SYRINGE

FIELD OF THE INVENTION

This invention relates to a safety device for connection of a syringe to the mouth or opening of a bottle containing a medicine or drug or a small tube for drug delivery from the syringe.

BACKGROUND OF THE INVENTION

There are substances with high environment risk, such as drugs of high toxicity, which are normally enclosed in small sealed bottles, having blocked on the mouth or opening thereof a rubber plug which can be perforated by a needle applied on a syringe in order to draw the drug or substance, in the case after injection of a solvent into the bottle, for later use of such a substance, for example for intravenous transfusion, if a drug is involved.

As mentioned, some of these substance are highly toxic or of high environment risk, so that it is highly desirable to prevent that even minimal small drops of the drug or substance would contaminate the outer ambient or come in contact with the skin of the person drawing the substance from the bottle.

At present, drawing of the substance or drug from a bottle of this type occurs by making the drug drawing person to wear rubber gloves and paying maximum attention in transfer step of the syringe with needle from the bottle to the successive use. There are also quite complex apparatuses, practically comprising watertight chambers in which liquid drawing is effected by operating the syringe and bottle from outside, commonly used in large hospitals for handling high risk substances. However, there is no warranty of avoiding an outside dripping of the liquid (substance or drug) between the drawing step from the bottle and the direct use step.

Many kinds of devices have been proposed for overcoming the above referred drawbacks.

The U.S. Pat. Nos. 3,392,726; 3,826,260; and 3,995,630 and the German Pat. No. 1,166,419 disclose devices suitable to connect an injection syringe to a vial which contains a medicament. The devices include a first member which is fixedly or detachably connected to the vial and a second member which can be connected to the syringe, the two members forming a telescopic assembly such that when the syringe is pressed toward the vial, a hollow needle perforates one or more seals thereby communicating with and between the interiors of the syringe and the vial. It can be easily seen that no provision is made for preventing accidental telescoping movement of the mentioned assembly and especially that no means are provided for avoiding the risk of contamination or the like when the two members are disconnected the one from the other in order to administer into a patient the dissolved medicament.

The U.S. Pat. No. 3,336,924 concerns a device which is similar to those mentioned hereabove, but in which the needle is protected by a covering which is fractured on telescoping movement of the parts. However, this device does not avoid the risk of contamination after the mixed vial contents has been aspired into the syringe and the syringe has been separated from the vial.

The U.S. Pat. No. 2,847,995 and the Norwegian Pat No. 141,537 disclose transfusion needle sheets maintaining the needle in properly sterile condition for indefinite periods of time.

OBJECTS OF THE INVENTION

It is the primary object of the present invention to provide a safety device applicable to a syringe and with a needle which is normally enclosed within a closed sealed chamber. The device is applicable to a bottle and is steadily restrainable thereon. The needle can be cauesd to exit from said chamber, perforating first a seal plug and then a plug applied to the bottle. However, the needle can be caused to exit from said chamber only when the device is mounted in an irremovable fashion on the bottle mouth or opening. Thus, the device cannot be disconnected from the bottle unless the needle has been caused to reenter the sealed chamber defined by the device. Accordingly, the liquid is prevented from dripping to pollute the external environment.

It is another object of the invention to provide a device of the above type which is of simple structure and can be subsequently used for connection to a plurality of different bottles, thereby enabling the user to draw into the syringe the contents of more than one bottle or to mix in the syringe liquids of different natures, such as different drugs or medicines.

SUMMARY OF THE INVENTION

These and further objects are achieved by a safety device comprising an elongate inner body defining a cylindrical cavity at one end of which a seat is formed for housing the free end of a syringe, an intermediate body having a hollow cylindrical extension which is housed and movable within the cavity of the inner body, a retaining element limiting the displacement between two end-of-stroke positions for the intermediate body relative to the inner body, a shaped resilient plug tightly closing the outward facing end of the cavity of said cylindrical extension, the other end of which opens into the cavity of of the inner body, a seat for housing the mouth or opening of a bottle or a small tube formed at the free end of the intermediate body, with said resilient plug projecting at the center of said seat, at least one flexible extension integral with said intermediate body and having a shaped portion thereof projecting to said housing seat for the mouth or opening of the bottle, an outer body superimposed to said intermediate and inner bodies, members restraining the outer body to the intermediate body allowing a mutual displacement between a position at which said extension is allowed to deflect or bend outwardly, and a position at which the outer body interferes with said extension, preventing the outward deflection or bending thereof, elements restraining to the inner body both the outer body and the intermediate body, enabling the axial displacement of these last two mentioned bodies with respect to the inner body only when the outer body is at the position where it interferes with said extension, preventing the outward deflection or bending thereof, the cavities of said intermediate and inner bodies being adapted to house a hollow needle, which can be connected to a syringe inserted in said seat of the inner body, the tip of said needle being positioned adjacent said resilient plug under rest or inoperative conditions of the device.

BRIEF DESCRIPTION OF THE DRAWINGS

For a clearer understanding of the structure and features of the device, an embodiment thereof will now be described, by mere way of unrestrictive example, with reference to the accompanying drawings, in which.

DETAILED DESCRIPTION OF THE PRESENTLY PREFERRED EMBODIMENTS

Figure 1:
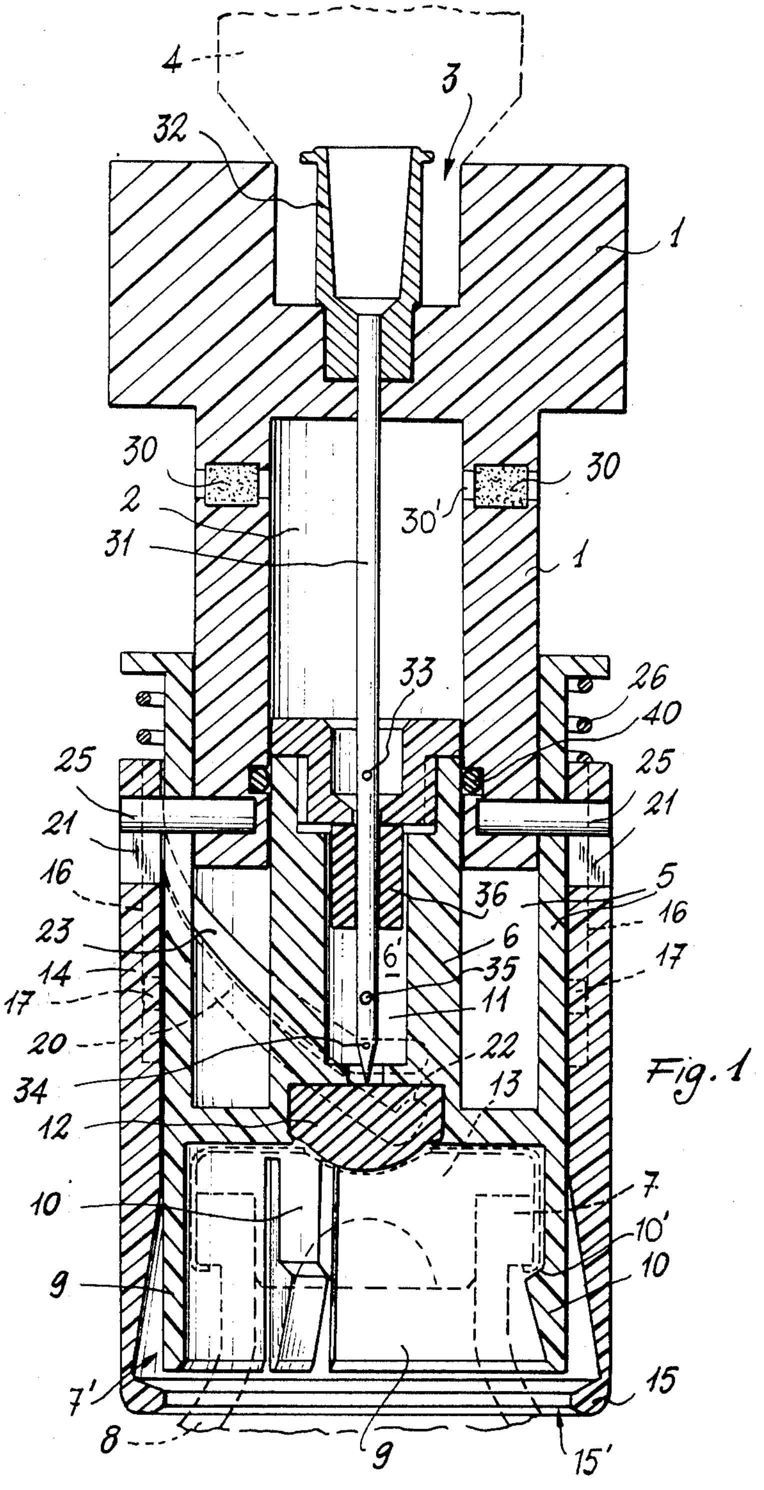
FIG. 1 is an enlarged axial sectional view showing the device at rest or inoperative condition.

The device shown in the above figures of the accompanying drawings comprises an elongate inner body 1 containing a cylindrical cavity 2. At one end of the elongate inner body 1 is a seat 3 is formed for housing the free end of a syringe 4. An intermediate body 5 has a hollow cylindrical extension 6 which is housed and movable within the cavity 2 of the inner body 1. At the lower free end (as seen in FIG. 1) of the intermediate body 5, a seat 7' is formed for housing the mouth opening 7 of a bottle 8. The seat 7' is defined by a cylindrical wall 9 of the intermediate body 5. The cylindrical wall 9 is interrupted or discontinued to comprise (in the case shown on the drawings) three distinct flexible extensions 10 located at 120° from one another. Two of the flexible extensions 10 are shown in FIG. 1, while only one of the flexible extensions 10 has been shown for simplicity in FIGS. 3 to 5.

As particularly shown in FIG. 1, each of the flexible extensions 10 has a tooth-shaped portion 10' thereof projecting inwardly of the seat 7' for the bottle mouth or opening 7. The tooth-shaped portions 10' are intended to be connected below the bottle mouth or opening 7 at the use conditions of the device, as shown in FIG. 1 and FIGS. 3 to 5.

The hollow cylindrical extension 6 contains a cavity 11 which is closed at the bottom by a shaped resilient plug 12 tightly closing the outward facing end of the cavity 11. The plug 12 is shaped and has an outwardly projecting portion thereof at the center of the seat 7'. The shaping of the plug 12 is such that, when a bottle is inserted in the seat 7', the plug 12 is firmly pressed against the outer surface of a rubber plug 13 which is mounted on the mouth or opening 7 of all the bottles of this type, such as those used for containing a drug or medicine. By pressing on the plug 13, the plug 12 slightly downwardly deforms the plug 13 (as shown in FIG. 1), preventing an empty chamber or space from being formed between the opposite surfaces of the two plugs.

The device also comprises an outer body 14 which surrounds the inner body 1 and the intermediate body 5. The outer body 14 is substantially in the shape of a hollow cylinder. The low portion of the outer body 14 adjacent the seat 7' for the bottle mouth or opening 7 is shaped so as to have an inner enlargement adjacent the extensions 10. The body 14 has an end free lip 15 of continuous annular shape. The lip 15 surrounds a hole 15' having a diameter substantially equal to the outer diameters of the cylindrical wall 9 and the flexible extensions 10.

The intermediate body 5 and the outer body 14 can move axially relative to each other, but they are inhibited from rotating relative to each other, since the outer body 14 has formed therein longitudinal straight grooves 16 in which teeth 17 outwardly projecting from the intermediate body 5 are inserted and longitudinally movable.

Two elongate slits or windows 20 are formed in the outer body 14. The slits 20 extend helicoidally in the direction of the axis of the device and have end portions 21 and 22, respectively, which are inclined relative to the remaining portions of the slits 20. The end portions 21 and 22 are more arranged in the direction of the axis of the device, as better explained in the following.

The intermediate body 5 similarly has two slits or windows 23 formed therein. The profiles of the slits 23 are, with the exception noted below, fully similar to the profiles of the slits 20, and the slits 23 can be superimposed over the slits 20. The sole exception (that is, the sole difference in shape between the slits 20 and the slits 23) is that the slits 23 do not have portions with different angling or inclination similar to the portions 21 and 22 of the slits 20.

Two pins 25 project from the inner body 1 and extend through the slits 23 and into the slits 20, thus mounting the intermediate body 5 and the outer body 14 on the inner body 1. It can also be seen that a compression spring 26 is interposed between the bodies 5 and 14. The compression spring 26 biases the outer body 14 towards the position shown in FIG. 1.

From the drawings it can also be seen that the wall defining the cylindrical cavity 2 in the inner body 1 has formed therein holes 30' closed by sterile filters 30. The filters 30 allow the passage of air and gases, but prevent any passage of powders, liquids, or microorganisms. Such filters are per se well known and commonly used in the pharmaceutical field.

In the embodiment shown, a hollow needle 31 is integral with the inner body 1. The hollow needle 31 has a mouth or opening 32 of any known type to which the free end of the syringe 4 can be restrained when inserted in the seat 3 of the inner body 1. The free end of the hollow needle 31 is closed, but three distinct holes 33, 34, and 35 are formed in the hollow needle 31. The holes 33 and 34 are of a very small size, so as to allow the passage of gases or air only, while the holes 35 is of a larger size and allows the passage of liquids.

A cavity 6' in the hollow cylindrical extension 6 accommodates therein a shaped gasket 36. The shaped gasket 36 is in sealing contact with the needle 31, but is not in contact with the wall of the hollow cylindrical extension 6.

Under rest or inoperative conditions, the device is with its various component parts arranged as shown in FIG. 1. The needle 31 is completely isolated from the external environment owing to the provision of plug 12, filters 30, and an annular gasket 40 sealing between the inner body 1 and the hollow cylindrical extension 6. Under these conditions, the mouth or opening 7 of a bottle holding, for example, a high risk drug for the ambient, can be inserted in the seat 7'. During this insertion, the flexible extensions 10 are deflected outwardly. Such a deflection is allowed because, adjacent the flexible extensions 10, the inner surface of the outer body 14 is outwardly flared, as clearly shown in FIG. 1.

At the end of the operation for introducing the bottle mouth or opening 7 into the seat 7', the tooth-shaped portions 10' of flexible extensions 10 are brought to connection below the mouth or opening 7, as shown in FIG. 1. In this condition, the compression spring 26 holds the outer body 14 and the intermediate body 5 apart, and the pins 25 are arranged in the end potins 21 of the slits 20. Since the end portions 21 of the slits 20 extend longitudinally, the rotation of outer body 14 relative to inner body 1 is prevented. Accordingly, the rotation of the intermediate body 5 relative to the inner body 1 is also prevented, since the intermediate body 5 can only slide longitudinally of the outer body 14 due to the cooperation of the longitudinal straight grooves 16 with the teeth 17.

Figure 3:
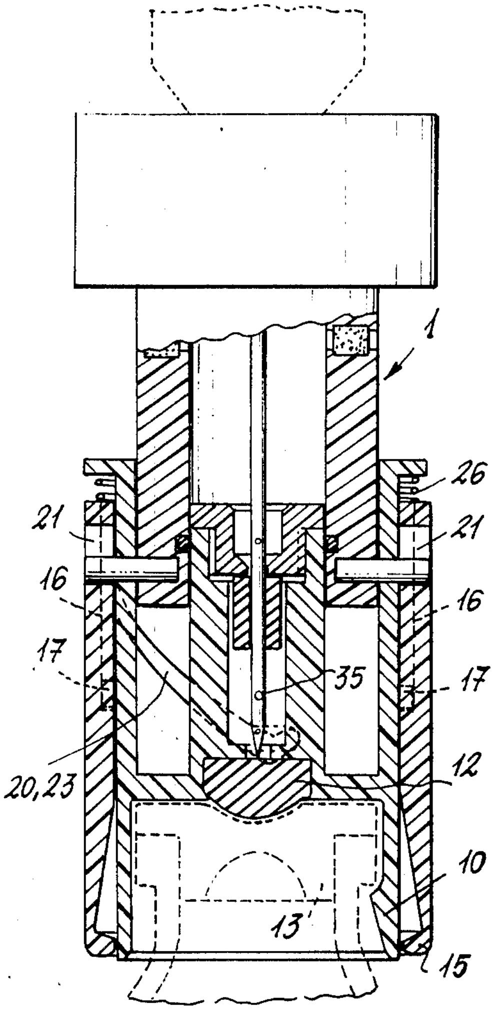
FIGS. 3 and 4 are two fragmentary axial sectional views of the device at two different working positions.

Now, by exerting a force on the outer body 14 or the inner body 1 to compress the compression spring 26, the pins 25 are moved longitudinally in the end portions 21 of the slits 20, thus bringing the pins 25 to the point where the slits 20 begin to overlap with the helicoidally inclined sections in the similarly shaped slits 23 on the intermediate body 5. Thus, the position shown in FIG. 3 is attained. It can be seen in FIG. 3 that the slits 20 and the slits 23 are effectively superimposed over each other and that the lip 15 of the outer body 14 has been moved to the level of the free ends of the flexible extensions 10. Therefore, the flexible extensions 10 are prevented from deflecting outwardly, and accordingly it is impossible to remove the bottle mouth or opening 7 from its seat 7', since the tooth-shaped portions 10' of the flexible extensions 10 steadily hold the mouth or opening 7.

Figure 4:
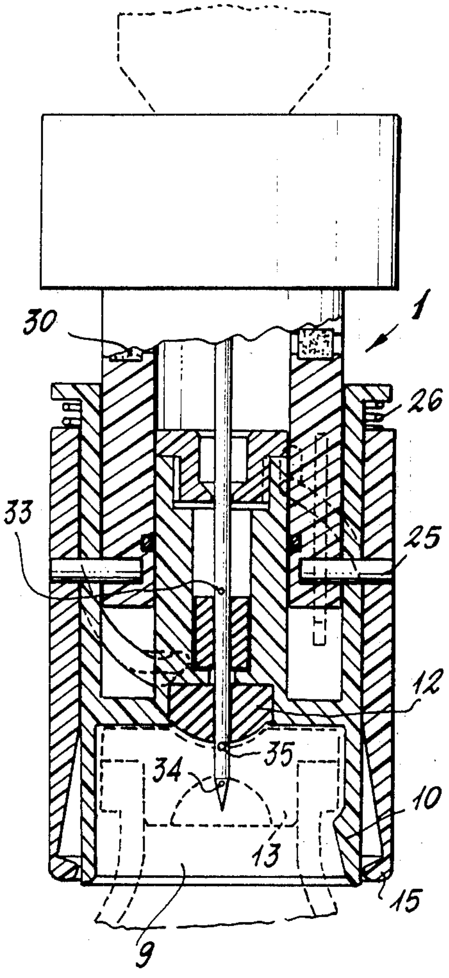

From this position (FIG. 3), when the helical slits 20 and 23 are superimposed over one another, the intermediate body 5 and the outer body 14 can be rotated as a unit (since they are integrally restrained relative to each other) relative to the inner body 1. The helical shape of the slits 20 and 23 causes the inner body 1 to move axially towards the intermediate body 5 and the outer body 14, thus causing the tip of the hollow needle 31 to be forced into the plug 12. As a result, the plug 12 is perforated by the hollow needle 31, the advancement of which continues until it also perforates the rubber plug 13 of the bottle 8 (as shown in FIG. 4).

At a first step of the axial movement of the hollow needle 31 relative to the plug 12 (FIG. 4), the hollow needle 31 draws the gasket 36 downwardly. When the hole 34 moves beyond the rubber plug 13 of the bottle 8, any pressure gas within the bottle 8 exits through the hole 34, passes through the needle cavity, exits therefrom through the hole 33, and is then exhausted to the outside through the filters 30. Similarly, should the bottle be under a vacuum, the outer air would penetrate into the bottle 8 for equalizing the pressure thereof, passing through the filters 30, the hole 33, and then the hole 34.

Figure 5:
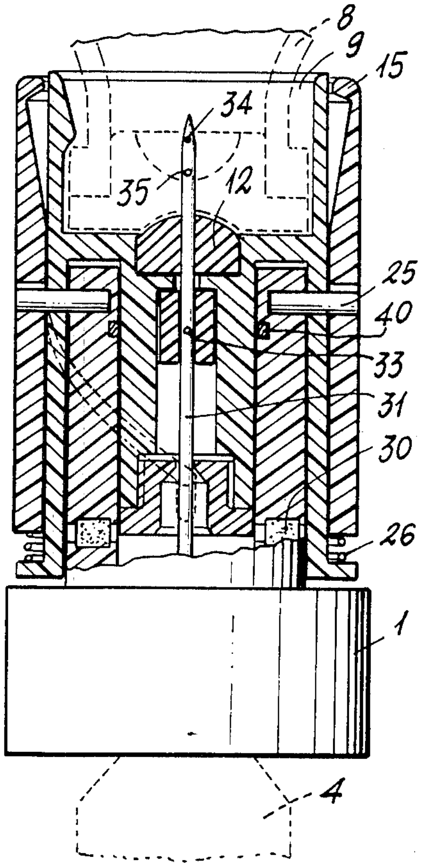
FIG. 5 is also a fragmentary axial sectional view showing said device at the condition in which it is during the step of drawing a liquid from a bottle, the device being shown rotated through 180° with respect to the position of the same in FIGS. 1 to 4.
Figure 2:
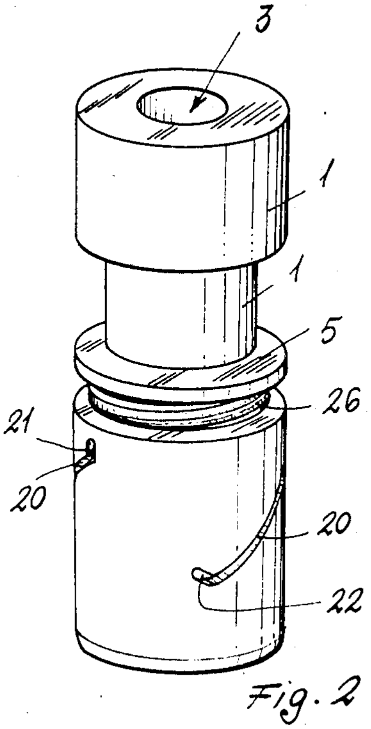
FIG. 2 shows the same device at the condition of FIG. 1, but in a top perspective view.

Further continuing the rotation of the intermediate body 5 and the outer body 14 relative to the inner body 1, the hollow needle 31 penetrates further through the plug 12 until the hole 35 is also arranged below the rubber plug 13—that is, until the body 35 is within the bottle 8. This position is shown in FIG. 5, wherein the device has been shown overturned (that is, rotated through 180° with respect to the positions shown in FIGS. 1 to 4) for a clearer explanation of the operation thereof.

Since at this position the hole 33 is closed by the gasket 36, the liquid contained in the bottle 8 can be drawn from the bottle 8 by the syringe 4. The liquid passes through the hole 35, into the needle cavity, and thence directly enters the syringe 4. Of course, it is also possible to introduce a liquid, such as a solvent, from the syringe 4 into the bottle 8 without any possible overflowings of even minimal amounts of liquid to the outside, since the shaped plug 12 is held firmly pressed at the center of the rubber plug 13 provided on the bottle 8.

Figure 6:
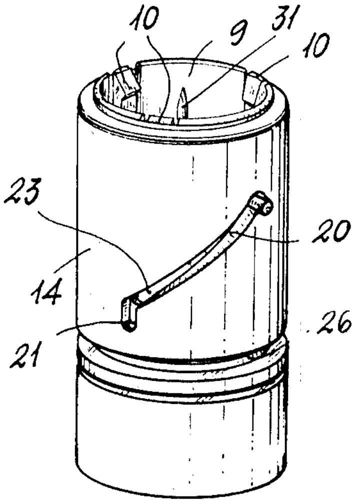
FIG. 6 shows the device at the condition of FIG. 5, but in a bottom perspective view.

Under these conditions (FIG. 5), when the hollow needle 31 projects beyond the sealing plug 12, it is impossible to separate the bottle 8 from the device. The connection of the device to the bottle 8 is stable owing to the provision of the end portions 22 of the slits 20 into which the pins 25 project (as shown in FIG. 6). Thus, the outer body 14 is axially displaced with respect to the intermediate body 5, and accordingly the slits 20 are displaced relative to the slits 23, so that the outer body 14 cannot be rotated together with the intermediate body 5 relative to the inner body 1.

For disconnection of the bottle 8 from the device, the outer body 14 is manually longitudinally displaced relative to the intermediate body 5, overcoming the resitance of the compression spring 26, until the slits 20 and the slits 23 are brought into registry. Thus, the assembly of the intermediate body 5 and the outer body 14 can be rotated again relative to the inner body 1, causing the hollow needle 31 to retract relative to the plug 12, thereby sequentially returning the device to the position shown in FIG. 4, then to the position shown in FIG. 3, and finally to the position shown in FIG. 1. In the latter position, the pins 25 once again penetrate into the end portions 21 of the two slits 20, the slits 20 and the slits 23 are no longer superimposed over one another, and the intermediate body 5 and the outer body 14 thus cannot be rotated relative to the inner body 1. Thus, the inadvertent downward movement of the hollow needle 31 relative to the plug 12 is once again prevented.

Having returned to the initial position of FIG. 1, it is thus possible by simply exerting a longitudinal tractive action to disconnect the bottle 8 from the device (by which action the outward deflection of the flexible extensions 10 is caused), after which the device can be coupled and restrained to a new bottle or to the opening of a small tube connected, for example, to an epicranial needle or the like, the opening of the small tube being of a shape entirely similar to that of the bottle.

From the foregoing it clearly appears that the hollow needle 31 can pass through the plug 12 only when the device is in the locking position of FIGS. 3 to 5, so that it is impossible to disconnect the device from the bottle 8 when the free end of the hollow needle 31 is still projecting beyond the rubber plug 13 of the bottle, or also merely beyond the sealing plug 12 of the device. It is also evident that a ratchet, a hook, or a similar expedient could be provided for preventing any axial translation of the outer body 14 with respect to the intermediate body 5 unless the bottle mouth or opening 7 is arranged within the seat 7'. Such an arrangement would make it absolutely impossible to cause the exit of the the tip of the hollow needle 31 from the plug 12 unless a bottle 8 is connected to the safety device. Such an expedient is not herein shown because it can be easily implemented by any person skilled in the art and in many different ways from one another, and also because it is not strictly essential for a good operation of the device herein claimed.

Finally, in order to cause the hollow needle 31 to exit beyond the plug 12, it is first essential to manually displace the outer body 14 relative to the intermediate body 5 while overcoming the action of the compression spring 26, then to translate the assembly of the outer body 14 and the intermediate body 5 in longitudinal direction relative to the inner body 1. Moreover, during the relative movement of the parts of the safety device, the bottle 8 is steadily restrained to the device and is disconnectable therefrom only after the hollow needle 31 has been withdrawn into the interior of the cavity 2 and the cavity 11.

It is evident that the slits 20 and 23 may have a different profile from that shown on the drawings, For example, they may be of a shape extending longitudinally along the device, with the ends of the slits 20 in the outer body 14 extending in the transverse direction.

It is also evident that, while achieving the same objects, the connection between the outer and intermediate bodies may be different from that shown. For example, the outer body 14 may be of cylindrical shape and having openings that can positioned at the flexible extensions 10, thereby enabling the flexible extensions 10 to be deflected outwardly. By rotating the outer body 14 relative to the intermediate body 5, the openings can be moved away from the flexible extensions 10, which will come to bear against the wall of the outer body 14, which thereby prevents the deflection thereof and thus prevents the bottle mouth or opening 7 from being moved away from the seat 7'.

Where the interior of bottle 8 is neither under pressure nor vacuum, no equalization is required for the inner pressure thereof with the external pressure. In that case, the hollow needle 31 may be of conventional shape—that is, open at its free end, without any provision of holes 33, 34, and 35. In this case, the provision of a gasket 36 is also not required, since the gasket 36 is only intended to close the hole 33 when liquid is drawn from or introduced into the bottle 8 by the syringe 4.

Finally, it will be appreciated that, although in the embodiment shown the gasket 36 has been shown as slidable on the outer surface of the hollow needle 31, the same results can be achieved by suitably dimensioning and shaping such a gasket and blocking it at a fixed position within the cavity 11 of the hollow cylindrical extension 6.

We claim:

1. A safety device for connection of a syringe to the mouth or opening of a bottle containing a drug or a small tube for drug delivery from the syringe, comprising an elongated inner body defining a cylindrical cavity, at one end of which a seat is formed for housing the free end of a syringe, an intermediate body having a hollow cylindrical extension which is housed and movable within the cavity of the inner body between a first end of stroke position defined by a retaining element limiting relative displacement of said inner body and said intermediate body in a first direction and a second end of stroke position defined by a retaining element limiting relative displacement of said inner body and said intermediate body in a second direction, opposite to the first direction, a shaped resilient plug sealingly closing the outward facing end of the cavity of said cylindrical extension, the other end of which opens into the cavity of the inner body, a housing seat for the mouth or opening of a bottle or a small tube formed at the free end of the intermediate body with said resilient plug projecting at the center of said seat, at least one flexible extension integral with said intermediate body and having a shaped portion thereof projecting to said housing seat for the bottle mouth or opening, an outer body superimposed to said intermediate and inner bodies, members restraining said outer body to the intermediate body enabling a mutual displacement between a position at which said extension is allowed to outwardly deflect, and a position at which the outer body interferes with said extension preventing the outward deflection thereof, elements restraining both said outer body and said intermediate body to the inner body, enabling the axial displacement of said outer body and said intermediate body relative to the inner body only when the outer body is located at the position at which it interferes with said extension preventing the outward deflection thereof, the cavities of said intermediate and inner bodies being adapted to house a hollow needle which can be connected to a syringe inserted in said seat of the inner body, the tip of said needle being positioned adjacent said resilient plug at the inoperative condition of the device and the top of said needle protruding through said resilient plug at the operative condition of the device.

2. A device as claimed in claim 1, wherein said retaining element of the intermediate body on the inner body and said elements restraining both the outer body and said intermediate body to the inner body comprise at least one elongate slit or window in the outer body and at least one elongate slit or window in the intermediate body, and at least one pin radially projecting from the inner body into said slits or windows, said at least one elongate slit or window in the outer and inner bodies extending in the direction of the longitudinal axis of the device and being superimposable to one another, except for the ends of the slit or window of the outer body which are shaped for enabling said outer body to axially move relative to the intermediate body, at least one spring being positioned between said outer and intermediate bodies, which spring holds the outer body axially urged away from the intermediate body.

3. A device as claimed in claim 2, wherein said outer and intermediate bodies are restrained to each other by a straight longitudinal groove in a first one of the two bodies facing the second one of the two bodies and by at least one tooth projecting from the second one of the two bodies towards the first one of the two bodies and housed and slidable in said straight longitudinal groove.

4. A device as claimed in claim 1, wherein said needle is integral with said inner body, and wherein there are provided three distinct, longitudinally spaced holes in communication with the inner cavity of the needle, the tip of the needle being closed, the intermediate hole being of a larger size than the other holes and such as to allow the passage of a liquid therethrough, while the other two holes are of somewhat reduced size, such as to allow the passage of a gas, the cylindrical extension of the intermediate body sealing on the surface of the cylindrical cavity of the inner body, the cylindrical wall of the cylindrical cavity of said inner body having formed therein at least one opening closed by a sterile filter, the needle having mounted thereon a gasket which is arranged in the cavity of said cylindrical extension of the intermediate body and relative to which said needle is longitudinally slidable, under the conditions in which the outer and intermediate bodies are superimposed to the maximum extent on the inner body, with said needle passing through said resilient plug and with the two holes of the needle closer to the needle tip projecting beyond said plug, said gasket being superimposed for sealing purposes on the one of said three longitudinally spaced holes which is farthermost from the needle tip.

5. A safety device for connection of a syringe to the mouth or opening of a bottle containing a drug or a small tube for drug delivery from the syringe, characterized in that it comprises an elongate inner body defining a cylindrical cavity, at one end of which a seat is formed for housing the free end of a syringe, an intermediate body having a hollow cylindrical extension which is housed and movable within the cavity of the inner body, a shaped resilient plug sealingly closing the outward facing end of the cavity of said cylindrical extension, the other end of which opens into the cavity of the inner body, a housing seat for the mouth or opening of a bottle or a small tube formed at the free end of the intermediate body with said resilient plug projecting at the center of said seat, at least one flexible extension integral with said intermediate body and having a shaped portion thereof projecting to said housing seat for the bottle mouth or opening, an outer body superimposed to said intermediate and inner bodies, members restraining said outer body to the intermediate body enabling a mutual displacement between a position at which said extension is allowed to deflect outwardly and a position at which the outer body interferes with said extension preventing the outward deflection thereof, elements restraining both said outer body and said intermediate body to said inner body, enabling the simultaneous displacement of said outer body and said intermediates body jointly relative to said inner body only when said outer body is located at the position at which it interferes with said extension preventing the outward deflection thereof, the cavities of said intermediate and inner bodies being adapted to house a hollow needle which can be connected to a syringe inserted in said seat of said inner body, the tip of said needle being positioned adjacent said resilient plug at the inoperative condition of the device and the tip of said needle protruding through said resilient plug at the operative condition of the device.

6. A device according to claim 5, wherein said members retaining said outer body to said intermediate body and said elements restraining both said outer body and said intermediate body to said inner body comprise a longitudinal slit in a first one of said outer and intermediate bodies and a tooth extending from a second one of said outer and intermediate bodies and sliding in said slit, and members restraining said inner body to said intermediate body allowing for the latter to rotate and simultaneously longitudinally translate with respect to said inner body, said bodies comprising at least a helicoidal slit formed in one of the two bodies and a pin rigid with said inner body or with said outer body and radially extending in said slit, said pin extending in a seat formed in said outer body or respectively in said inner body in such a way as to allow for said outer body to translate in a limited degree both with respect to said intermediate body and said inner body at the end of stroke positions of said intermediate body with respect to said inner body between said outer body and said intermediate body, there being arranged a spring which biases said outer body longitudinally away from said intermediate body.

7. A device according to claim 6, wherein a helicoidal slit is formed in said outer body and a like helicoidal slit is formed in said intermediate body, said pin being rigid with said inner body and extending within said slits, the ends of said slit formed in said outer body being slanted longitudinally of the device.

8. A device as claimed in claim 5, wherein said needle is integral with said inner body, and wherein there are provided three distinct, longitudinally spaced holes in communication with the inner cavity of said needle, the tip of said needle being closed, the intermediate hole being of a larger size than the other holes and such as to allow the passage of a liquid therethrough, while the other two holes are of somewhat smaller size, such as to allow the passage of a gas, the cylindrical extension of said intermediate body sealing on the surface of the cylindrical cavity of said inner body, the cylindrical wall of the cylindrical cavity of said inner body having formed therein at least one opening closed by a sterile filter, said needle having mounted thereon a gasket which is arranged in the cavity of said cylindrical extension of said intermediate body and relative to which said needle is longitudinally slidable, under the conditions in which said outer and intermediate bodies are superimposed to the maximum extent on said inner body, with said needle passing through said resilient plug and with the two holes of said needle closer to the needle tip projecting beyond said plug, said gasket being superimposed for sealing purposes on the one of said three longitudinally spaced holes which is farthest from the needle tip.

* * * * *